United States Patent [19]

Tomich et al.

[11] Patent Number: 5,240,837
[45] Date of Patent: Aug. 31, 1993

[54] CDNAS ENCODING SOMATOTROPIN, EXPRESSION VECTORS AND HOSTS

[75] Inventors: Che-Shen C. Tomich; Eric R. Olson; John E. Mott, all of Kalamazoo, Mich.

[73] Assignee: The Upjohn Company, Kalamazoo, Mich.

[21] Appl. No.: 438,465
[22] PCT Filed: Feb. 9, 1988
[86] PCT No.: PCT/US88/00328
 § 371 Date: Aug. 18, 1989
 § 102(e) Date: Aug. 18, 1989
[87] PCT Pub. No.: WO88/06186
 PCT Pub. Date: Aug. 25, 1988

Related U.S. Application Data

[63] Continuation-in-part of Ser. No. 16,294, Feb. 19, 1987, abandoned.

[51] Int. Cl.$^5$ .................. C07H 21/00; C12N 15/18; C12N 15/69; C12N 15/70
[52] U.S. Cl. ............... 435/172.3; 435/252.33; 435/320.1; 536/23.51; 536/24.1; 935/27; 935/29; 935/41; 935/42
[58] Field of Search ............. 435/69.4, 172.3, 252.33, 435/320.1, 849, 172.1, 23.51, 24.1; 530/399; 536/27, 23.51, 24.1; 935/27, 29, 41, 42

[56] References Cited

U.S. PATENT DOCUMENTS

| 4,511,502 | 4/1985 | Builder et al. .................. 260/112 R |
| 4,511,503 | 4/1985 | Olson et al. ..................... 260/112 R |
| 4,512,922 | 4/1985 | Jones et al. ..................... 260/112 R |
| 4,518,526 | 5/1985 | Olson ............................... 260/112 R |
| 4,758,512 | 7/1988 | Goldberg . | |

FOREIGN PATENT DOCUMENTS

| 075444 | 9/1980 | European Pat. Off. . |
| 103395 | 8/1983 | European Pat. Off. . |
| 0111814 | 6/1984 | European Pat. Off. . |
| 131843 | 7/1984 | European Pat. Off. . |
| 0121386 | 10/1984 | European Pat. Off. . |
| 0125818 | 11/1984 | European Pat. Off. . |
| 0136490 | 4/1985 | European Pat. Off. . |
| 159123 | 8/1985 | European Pat. Off. . |
| WO85/03949 | 9/1985 | PCT Int'l Appl. . |
| 2073245 | 3/1980 | United Kingdom . |

OTHER PUBLICATIONS

Wright, E. M. et al., "Dual-Origin Plasmids Containing an amplifiable ColE1Ori" *Gene* 49:311-321 (1986).

Federation Proceedings, vol. 45, No. 3, Mar. 1986, Federation of American Societies for Experimental Biology (US), p. 174.

Chemical Abstracts, vol. 99, Aug. 1983, (Columbus, Ohio, US) B. E. Uhlin et al.: "New runaway replication-plasmid cloning vectors and suppression of runaway replication by novobiocin," p. 177, abstract 65339f.

B. E. Uhlin et al.: "New runaway replication-plasmid cloning vectors and suppression of runaway replication by novobiocin." Gene, 22, 255-65, (1983).

D. V. Goeddel et al., Direct expression in *Escherichia coli* of a DNA sequence coding for human growth hormone, Nature, 281:544-548 (1979).

P. H. Seeburg et al., Efficient Bacterial Expression of Bovine and Porcine Growth Hormones, DNA, 2:37-45 (1983).

(List continued on next page.)

Primary Examiner—Robert A. Wax
Assistant Examiner—Dian Jacobsons
Attorney, Agent, or Firm—Paul J. Koivuniemi; Gregory W. Steele; James D. Darnley, Jr.

[57] ABSTRACT

This invention discloses novel species of cDNAs encoding somatotropins, novel dual replicon vectors, hosts for such vectors and hosts for expressing the somatotropins encoded by such cDNAs.

16 Claims, No Drawings

OTHER PUBLICATIONS

A. C. Paladini et al., Molecular Biology of Growth Homone, CRC Reviews in Biochem., 15(1):25–56 (1983).

P. J. Eppard and D. E. Bauman, The Effect of Long-Term Adminstration of Growth Hormone on Performance of Lactating Dairy Cows; and Effect of Growth Hormone on Growth Rates and Mammary Development of Ruminants, Proc. 1984 Cornell Nutrition Conference for Feed Manufacturers, pp. 5–17, published by Cornell University, Ithaca, New York.

B. E. Schoner et al., Role of mRNA translational efficiency in bovine growth hormone expression in *Escherichia coli*, PNAS USA, 81:5403–5407 (1984).

R. G. Schoner et al., Isolation and Purification of Protein Granules from *Escherichia Coli* Cells Overproducing Bovine Growth Hormone, Bio-Tech., 3:151–154 (Feb. 1985).

5,240,837

CDNAS ENCODING SOMATOTROPIN, EXPRESSION VECTORS AND HOSTS

This application is the U.S. national phase of international application PCT/US88/00328, filed Feb. 9, 1988 which is a continuation-in-part of U.S. patent application Ser. No. 07/016,294, filed Feb. 19, 1987, now abandoned.

FIELD OF THE INVENTION

This invention relates to the expression of heterologous polypeptides. More specifically, the invention discloses novel cDNAs encoding somatotropins which are expressed at high levels in E. coli. A generic expression system comprising a mutated E. coli host cell and an expression vector having a dual replicon arrangement also is disclosed herein.

INFORMATION DISCLOSURE

Expression of somatotropins from a variety of animals by transformed microorganisms is known (Goeddel, D. V. et al., "Direct Expression in *Escherichia coli* of a DNA sequence coding for human growth hormone", Nature, 281:544-548 (1979); and Seeburg, P. H. et al., "Efficient Bacterial Expression of Bovine and Porcine Growth Hormones", DNA, 2:37-45 (1983)).

Naturally occurring bovine somatotropin (BSt) is a mixture of heterogeneous proteins, the amino acid sequences of which are known (Paladini, A. C., et al., Molecular Biology of Growth Hormone, CRC Reviews in Biochem., 15(1):25-56 (1983)). The naturally occurring mixtures have been purified from pituitary glands of cattle. The commercial potential for the use of BSt for promoting growth and lactation is well recognized and documented by biological studies on both dairy and feed cattle (Eppard, P. J. and Bauman, D. E., The Effect of Long-Term Administration of Growth Hormone on Performance of Lactating Dairy Cows; and Bauman, D. E., Effect of Growth Hormone on Growth Rates and Mammary Development of Ruminants, Proc. 1984 Cornell Nutrition Conference for Feed Manufacturers, pp. 5-17, published by Cornell University, Ithaca, N.Y.).

Recobinant bovine somatotropin (rBSt) can be produced in transformed microorganisms using a variety of recombinant genetic plasmids (European Patent Application 47 600; United Kingdom Patent Application, GB 2073245A; and Schoner, B. E. et al., Role of mRNA Translational Efficiency in Bovine Growth Hormone Expression in *Escherichia coli*, Proc. Natl. Acad. Sci. USA, 81:5403-5407 (1984)).

Analogs of BSt are also known (European Patent Application 103 395; and Schoner, B. E., et al., supra). Unlike the present invention, these analogs of BSt relate to the insertion or deletion of bases at the 5' end of the BSt gene thereby creating a protein different from the naturally-occurring amino acid sequences. Modifications to rBSt cDNAs to maximize preferred codons include changing the first two native alanine codons of GCC to GCT (European Patent Application 111,814). However, EP 111,814 teaches that preferred codon substitution and reduction of secondary structure is critical towards optimizing expression. The instant invention demonstrates that many of these known changes are not necessary to achieve high levels of expression when the cDNAs are combined with a runaway-replicon-type plasmid.

Methods for culturing and fermenting transformed microorganisms expressing BSt are also known and fully described in the above-cited literature.

Purification of biologically active rBSt from transformed cells has also been described previously (U.S. Pat. Nos. 4,511,502; 4,511,503; 4,512,922; 4,518,526; European Patent Application 131 843; and, Schoner, R. G., et al., "Isolation and Purification of Protein Granules from *E. coli* Cells Overproducing BSt", Bio-Tech., 3:151-154 (1985)).

The instant invention discloses cDNAs encoding somatotropins and analogs of somatotropins that are expressed at high levels when compared to the native somatotropin cDNA. It is known that native cDNAs of porcine and bovine somatotropin are not expressed at commercially acceptable levels in most *E. coli* systems and that changes in the cDNA are required for such expression. Attempts to increase the percentage of preferred codons in the cDNA have had little affect and workers have had to resort to substantial modifications of the cDNA to reach acceptably high levels of expression. Seeburg, P. H. et al., DNA, 2:37-45 (1983) increased expression by eliminating the strong secondary structure resident after the condon for amino acid residue 11 in the native cDNA of bovine somatotropin (see also European patent application 75444). They postulated that eliminating the secondary stem loop structures would enhance expression; this work directs the reader's attention to regions of hydrogen bonding in excess of $-12K$ calories/mole.

The instant invention teaches that high levels of expression need not involve substantial base sequence alterations. Rather, by making minor basepair changes in the first four codons of the rBSt cDNA, one can effect a substantial increase in expression in nonrunaway plasmids. When coupled with runaway plasmids, the cDNAs of the instant invention are expressed at even higher, commercially acceptable levels. The use of runaway plasmids to express rBSt is known (European patent applications 159,123 and 111,814). Neither application discloses the exact DNA sequences disclosed herein for the amino terminus of rBSt.

European patent application 103,395 discloses that expression of rBSt in *E. coli* will be at least 100 times higher than for the native cDNA of BSt if the first three to nine triplet codons are deleted. EP application 103,395 also indirectly suggests the possibility of using point mutations in the early condons to eliminate secondary structural interference with the Shine-Dalgarno region, but concluded that such changes could not be achieved with significant affect without altering the primary amino acid sequence of that part of the BSt protein.

SUMMARY OF THE INVENTION

This invention relates to expression plasmids, preferably containing a runaway type replicon, useful for transforming E. coli host cells permitting the host cells to produce a somatotropin-like protein wherein the plasmid contains the cDNA encoding a somatotropin selected from the group consisting of bovine, porcine, ovine somatotropin, and analogs thereof, wherein the first four codons encoding the somatotropin are selected from the group consisting of:

GCC TTC CCA GCT;       a)

GCT TTC CCA GCT;       b)

-continued

| | |
|---|---|
| ACC TTC CCA GCC; | c) |
| GCC TTC CCA GTC; | d) |
| AAA TTC CCA GCC; | e) |
| TTC TTC CCA GCC; | f) |
| and, | |
| TTC CCA GCC ATG. | g) |

The preferred runaway-type replicons are those derived from R1 mutations commercially available from A/S Alfred Benzon of Copenhagen, Denmark. Specifically those replicons found in Benzon's pBEU# series, i.e., pBEU-50 or pBEU-17 which are identical runaway replicons. Most preferred are those expression plasmids in which the runaway replicon is placed in combination with the original replicon from pBR322. These chimeric plasmids produce exceptionally high level expression of somatotropins in *E. coli*. The preferred *E. coli* host cells are those carrying mutations of either the rpoH or the hflB gene (see below). Most preferred are those host cells carrying the rpoH112 or hflB29 alleles (see below).

The above-described expression plasmids having a dual replicon arrangement are of general use for the expression of heterologous genes and are particularly advantageous when combined with the preferred *E. coli* host cells having mutations in either the rpoH or hflB gene, preferably, the rpoH112 and hflB29 alleles. In addition to the expression of somatotropins, this combination of host and vector is useful for the expression of biologically important proteins such as chymosin, interferon or interferon-like proteins, interleukins, insulin, viral proteins, urokinase, colony stimulating factor, tumor necrosis factor, protein C and the like.

DEFINITIONS

The term "expression unit" means a DNA sequence containing a complete unit of gene expression and regulation, including structural genes, regulator genes and control elements which are necessary for transcription, translation and for recognition by regulator gene products.

The term "heterologous", when referring to a gene, indicates that the gene has been inserted into a host cell either by way of a stable plasmid or through integration into the genome, and, when referring to a protein, indicates that the protein is the product of a heterologous gene. Heterologous proteins are proteins that are normally not produced by a host cell or are normally produced in limited quantities.

"Native" refers to the sequence of amino acids or nucleic acids occurring from the natural source. A "native protein" is a protein having a primary structure identical with the naturally occurring protein. For an oligonucleotide or codon, the native nucleic acid sequence is identical to that occurring in nature, e.g., the basepair sequence of a cDNA synthesized from a naturally occurring mRNA would be the native sequence. For recombinant genes or proteins, the native sequence optionally includes the presence of the initiation codon ATG encoding methionine or a methionine residue present at the amino terminus.

"BSt" refers to bovine somatotropin which includes a heterogenous mixture of proteins having ala-phe-pro-ala-met or phe-pro-ala-met at the amino terminus. For purposes of this application, the first codon or residue will be considered to be alanine for numbering purposes. Related terms include bovine growth hormone, BGH, recombinant bovine somatotropin, or rBSt. Recombinant BSt may optionally have an additional methionine residue at its amino terminus.

"Replicons" refer to DNA sequences that control the replication of recombinant DNA cloning and expression plasmids.

"Runaway replicons" contain sequences which either lack, or can be induced to lose, copy number control. Such loss results in uncontrolled replication and an increase in the copy number of the DNA molecule into which the runaway replicon has been incorporated. Related terms include runaway-type plasmids or runaway plasmids which are plasmids containing runaway replicons.

"Somatotropin(s)" refers to mammalian, fish and avian growth hormones. Unless restricted by the term "native", the term "somatotropin(s)" includes analogs of these proteins wherein there is sufficient amino acid sequence identity to permit growth hormone activity to be maintained. Such analogs include recombinantly produced somatotropins having the same amino acid sequences as the heterogeneous species found in purified preparations from pituitary glands and analogs artificially created by modification of somatotropin encoding DNAs such as are described in European patent applications 103,395 and 75,444. In addition, in the primary sequence of rBSt, any L-amino acid may be substituted for a D-isomer thereof and various amino acids may be interchanged without affecting the activity of the molecule itself. Thus, for example, (1) alanine, leucine, isoleucine, valine and proline are interchangeable, (2) phenylalanine and tryptophan are interchangeable, (3) serine, threonine and tyrosine are interchangeable, (4) asparagine and glutamine are interchangeable, (5) lysine, arginine, histidine and ornithine are interchangeable, and (6) aspartic acid and glutamic acid are interchangeable.

"Transformed microorganism" refers to a prokaryotic or eukaryotic single celled organism containing or hosting a plasmid artificially inserted into the cell using techniques well known in molecular genetics.

DETAILED DESCRIPTION

This invention provides methods for preparing mutant cDNA sequences that result in high level expression of eukaryotic growth hormone genes in recombinant microorganisms. In particular, the construction of several cDNAs useful for obtaining high level synthesis in *E. coli* of mature bovine and porcine growth hormones in different vectors is illustrated. For comparison, amounts of products expressed are presented for plasmids containing BSt cDNAs with and without nucleotide changes. Table 1 sets forth the coding sequence of mature BSt cDNA and Table 2 sets forth the mutations introduced into the 5' region of the BSt cDNA to enhance expression when compared to the native cDNA. The oligonucleotides of Table 2 were synthesized chemically according to the methods set forth below.

A. General Methods

Generally, the definitions of nomenclature and descriptions of general laboratory procedures used for this invention can be found in Maniatis, T. et al., Molecular Cloning, A Laboratory Manual, Cold Spring Harbor Laboratory, Cold Spring Harbor, N.Y. (1982). The manual is hereinafter referred to as "Maniatis" and is incorporated herein by reference.

All *E. coli* strains are grown on Luria broth (LB), LB with glucose, Difco's Antibiotic Medium #2, or M9 medium supplemented with glucose and acid-hydrolyzed casein amino acids. Strains resistant to antibiotics are maintained at the drug concentrations described in Maniatis.

Transformations are performed according to the method described by Morrison, D. A., J. Bacteriol., 132:349-351 (1977), or by Clark-Curtiss, J. E. and Curtiss, R., Meth. Enzymol., 101:347-362 (1983).

All enzymes are used according to the manufacturer's instructions. Restriction fragments are separated by either agarose or polyacrylamide gel electrophoresis and isolated by electroelution (Maniatis) or by adsorption onto glass powder (Vogelstein, B. and Gillespie, D., Proc. Natl. Acad. Sci. USA, 76:615-619 (1979)).

Large scale and rapid plasmid isolations are done as described in Maniatis.

Protein concentration is determined using the BioRad protein assay kit, based on Coomassie Blue binding.

SDS polyacrylamide gel electrophoresis for protein analysis is performed as described in Morse, L., et al., J. Virol., 26:389-410 (1978), and Laemmli, U. K., Nature (London) 226:680-685 (1970).

Western immunoblotting analysis was performed as described in Towbin, H., et al., Proc. Natl. Acad. Sci. USA, 76:4350-4354 (1979).

Colony hybridization is carried out as generally described in Grunstein, M. et al., Proc. Natl Acad. Sci. USA, 72:3961-5 (1975). Filters are then thoroughly air dried and baked in vacuo for 2 hours at 80° C.

Hybridization conditions for oligonucleotide probes are as previously described by Goeddel, D. V. et al., Nature, 290:20-26 (1981). After hybridization, the probe containing solution is removed and saved and the filters are washed in 0.1% SDS, 5×SSC. Filters are air dried, mounted, and autoradiographed using Kodak X-OMAT AR film and Dupont Cronex Lightning Plus intensifying screens at $-70°$ C.

For sequencing plasmids, mini-lysates of plasmid DNA are prepared according to the method of Holmes, D. S. et al., Anal. Biochem., 114:193 (1981), or by the alkaline-lysis procedure described in Maniatis. Dideoxy sequencing is carried out according to Sanger, F. et al., J. Mol. Biol., 143:161-178 (1977) using double-stranded plasmids. The dideoxy-containing reactions are prepared for electrophoresing by heating to 90° C. for 2 min, and quenching on ice. 2-3 μl per lane is loaded on an 8% denaturing polyacrylamide gel prepared and run according to Sanger and Coulson, FEBS Lett., 87:107-110 (1978).

Nucleotide sizes are given in either kilobases (kb) or basepairs (bp).

Oligonucleotides that are not commercially available can be chemically synthesized according to the solid phase phosphoramidite triester method (Beaucage, S. L. and Caruthers, M. H., Tetrahedron Letts., 22(20):1859-1862 (1981)) using an automated synthesizer, as described in Needham-VanDevanter, D. R. et al., Nucleic Acids Res., 12:6159-6168 (1984). After the oligonucleotides are purified, they are desalted on a Waters Sep-Pak C18 column.

The sequence of the synthetic oligonucleotides is verified using the chemical degradation method of Maxam, A. M. and Gilbert, W., Methods in Enzymology, 65:499-560 (1980). Alternatively, the sequence can be confirmed after assembly of the oligonucleotide fragments into plasmids using the method of Maxam and Gilbert, supra, or the chain termination method for sequencing double-stranded templates of Wallace, R. B. et al., Gene, 16:21-26 (1981).

To assemble the oligonucleotides, the 5'-OH ends of the oligonucleotides to be ligated within the linker are phosphorylated with T4 polynucleotide kinase in the presence of 2 μCi of γ-$^{32}$P-ATP per μg of oligonucleotide, followed by a chase with an excess of unlabelled ATP. Annealing is performed in 50 mM Tris-HCl, pH 7.8, 10 mM MgCl$_2$, by heating to 90° C. for 10 min, followed by slow cooling to room temperature over a period of 2-4 h. After incubation at 15° C. for 1 h and addition of ATP to 0.5 mM, DTT to 20 mM, and 400 U T4 DNA ligase, the reaction mixture is incubated at 15° C. overnight. The correctly assembled linker is purified by 10% polyacrylamide gel electrophoresis using the labelled HaeIII digested φX174 DNA as a standard, followed by electroelution (Maniatis) and precipitation with ethanol.

B. Expression in Prokaryotes

To obtain high level expression of a cloned gene in a prokaryotic system, it is essential to construct expression vectors which contain, at the minimum, a strong promoter to direct mRNA transcription, and a ribosome binding site for translational initiation. Since the accumulation of large amounts of a gene product often inhibits cell growth and sometimes causes cell death, the promoter chosen to direct the synthesis of the product should be regulated in such a way that cell growth can be allowed to reach high densities before the induction of the promoter. Examples of regulatory regions suitable for this purpose are the promoter and operator region of E. coli tryptophan biosynthetic pathway and the leftward promoter of phage lambda ($P_L$). The trp promoter is repressed in the presence of tryptophan and can be induced by tryptophan starvation or by the addition of the inducer indole acrylic acid (Yanofsky, C., et al., J. Bacteriol., 158:1018-1024 (1984)). Promoter $P_L$ is controlled by the repressor cI. With a temperature-sensitive mutation in the cI gene, e.g., cI857, $P_L$ can be induced at temperatures above 38° C. (Herskowitz, I. and Hagen, D., Annu. Rev. Genet., 14:399-445 (1980)). Most preferred are expression vectors having restriction enzyme sites at an appropriate distance from the Shine-Dalgarno sequence in order to insert genes to be expressed.

To synthesize a protein encoded by a eukaryotic gene from its cDNA sequence in *E. coli* intracellularly, it is expedient to remove the 5' untranslated region and the sequence coding for the signal peptide and to supply an initiation codon for translation initiation of the sequence coding for the protein. It may also be necessary to replace some of the coding sequence for the protein with chemically synthesized oligonucleotides to maximize translation efficiency. The instant invention specifically describes a truncated BSt gene having the 5' untranslated region, the pre-sequence, and a 66 bp coding sequence for the beginning of mature BSt deleted. This truncated BSt sequence is cloned into our expression vector pTrp1 to yield plasmid pTrp-BStmlb. To complete the truncated BSt sequence for expression, oligonucleotides are inserted into pTrp-BStmlb. The oligonucleotides can be designed to incorporate changes leading to optimal expression with or without alteration in amino acid residues.

A preferred embodiment of this invention utilizes a high-copy number plasmid or a runaway-type origin of replication. All plasmids are known to contain a DNA sequence from which replication of the plasmid occurs. These sequences are diverse in nature and are generally referred to as origins of replication (ori) or replicons. In some cases the ori can function by using *E. coli* host proteins for replication, while others require additional protein factors encoded by the plasmid.

The number of copies of a plasmid per cell (i.e., copy number) can be affected by changes in the replication ori and in the regulation of the plasmid encoded genes. Vector mutations have been isolated which cause increased plasmid replication either constitutively or under controlled conditions. Examples of constitutively high-copy-number plasmids are pUC19 (Yanisch-Perron, C. et al., Gene, 33:103–119 (1985), available from Bethesda Research Labs, Gaithersburg, MD, USA); and pHC314 (Boros, I. et al., Gene, 30:257–260 (1984)). The increase in plasmid replication under controlled conditions is referred to as plasmid "runaway". The control mechanism is usually a shift in culture temperature. The preferred "runaway" vector system that is used here was derived from the R1 plasmid. Temperature sensitive mutations of vector derivatives of R1 were isolated in a two-step selection (Uhlin and Nordstrom, Mol. Gen. Genet., 165:167–179 (1978); and Uhlin et al., Gene, 6:91–106, (1979)). Upon heat induction these vectors can comprise as much as 75% of the total DNA in the cells.

The replication region of the R1 plasmid is clustered on about 2.5 kb of DNA sequence (Ryder et al., Gene, 17:299–310 (1982)). This region contains at least three genes and the origin of replication (Light and Molin, EMBO J., 2:93–98 (1983); Light et al., Mol. Gen. Genet., 198:503–508 (1985)). The genes are copB, copA, and repA. The production of the repA protein acts to initiate replication at the ori. The number of initiation events is proportional to the amount of the repA protein produced. The function of the copA and copB gene products is to regulate the amount of repA protein made. The copB product is a repressor molecule which binds to a repA specific promoter (Riise and Molin, Plasmid, 15:163–171 (1986); Givskov et al., Gene, 57:203–211 (1987)). The repA gene is also expressed from the upstream copB promoter. The copA gene has its own promoter transcribed in the opposite direction to copB and repA and produces an antisense RNA which hybridizes to the repA mRNA and decreases the efficiency of translational initiation of the repA mRNA.

The Benzon vectors used herein, such as pBEU-50 and pBEU-17, were derived from the original two-step temperature controlled runaway vector derived from R1 (Uhlin and Nordstrom, supra; Uhlin and Clark, In: Molecular Biology, Pathogenicity, and Ecology of Bacterial Plasmids, eds. S. B. Levy, R. C. Clowes and E. L. Koenig, Plenum Press, p. 670 (1981)). These vectors contain two promoter mutations. The first is a mutation in the copA promoter which reduces the amount of antisense copA RNA and the second is a mutation in the copB promoter which increases transcriptional initiation at elevated temperatures (Givskov et al., supra). *E. coli* cells containing the pBEU-50 vector are grown at temperatures of 30° C. or lower. When the cells are shifted to temperatures above 34° C. the plasmid copy number increases and this in turn amplifies the expression of genes which have been cloned into the vector (Uhlin et al., supra).

A chimeric vector composed of the pBR322 replicon and the runaway replicon of pBEU-17 expresses the modified somatotropins of the instant invention at particularly high levels. When placed in combination with two E. coli strains exhibiting low levels of protease activity, expression levels become extremely high.

Several genes in E. coli are known to affect the expression of proteases in the cell. These genes include lon, hflA, hflB, and rpoH (Cell, 41:587–595 (1985); Proc. Natl. Acad. USA 81:6647–6651 (1984); Proc. Natl. Acad. Sci. USA 81:6779–6783 (1984); Cell 31:565–567 (1982); Genetics 77:435–448 (1974)). Strains containing either a rpoH or hflB mutation have demonstrated enhanced expression of rBSt, as modified herein, and particularly in combination with a runaway plasmid. Preferred alleles are rpoH112 and hflB29. Other low protease strains are unable to enhance expression of rBSt.

Techniques for isolation and purification of mammalian somatotropins from recombinant microorganisms are well known in the art (see, e.g., U.S. Pat. Nos. 4,511,502, 4,512,922, 4,518,526; European Patent Application 131,843; and Schoner, R. G., et al., supra). In brief, the process involves lysing the cells, selective centrifugation, reshuffling of any non-native disulfide bonds to the native configuration and column chromatography.

Conventions used to represent plasmids and fragments in Charts 1–14 are as follows: the single line figures on the charts represent both circular and linear double-stranded DNA with translation initiation or transcription occurring in the direction of the arrow where indicated below a promoter or structural gene. Asterisks (*) represent the bridging of nucleotides to complete the circular form of the plasmids. Fragments do not have asterisks because they are linear pieces of double-stranded DNA. Endonuclease restriction sites are indicated above the line. Gene markers are indicated below the line. The relative spacings between markers do not indicate actual distances but are only meant to indicate their relative positions on the illustrated DNA sequence.

EXAMPLE 1

RBSt Expression in Non-runaway Vectors

A) The Expression Vector pTrpl

A prokaryotic expression vector for expressing heterologous proteins in microorganisms preferably has a strong regulatable promoter to mediate transcription and a strong ribosome binding site for translation initiation. For expression of mature BSt in E. coli, we have constructed the expression vector pTrpl which is derived from pSK4 (Kaytes, P. S., et al., J. Biotech., 4:205–218 (1986)). pTrpl contains the promoter and operator sequence of the E. coli tryptophan operon, the Shine-Dalgarno sequence of the trpL gene, the replication origin from pBR322 and a gene for ampicillin resistance. pTrpl has a unique ClaI site following the trpL Shine-Dalgarno sequence and a unique KpnI/Asp718 site immediately after the initiation codon, ATG. Insertion of a gene having an initiation codon at the ClaI site of pTrpl allows expression of that gene. Insertion of a gene at the KpnI/Asp718 site results in the expression of that gene as a fusion with amino acid gln or gln and val depending upon which site is used.

To make pTrpl, two complementary oligonucleotides are inserted into pSK4, as shown in Chart 1. Plasmid pSK4 contains the promoter/operator region of the trp operon and the trpL ribosome binding site cloned into pBR322 which also specifies resistance to ampicillin. The large BamHI/ClaI fragment including the trp sequences is cut out from pSK4 and purified by electroelution from agarose gels (fragment 1). Two complementary oligonucleotides are combined to form fragment 2. Fragment 2 has a ClaI and a BamHI sticky end at the 5'- and 3'-end, respectively, and is ligated to fragment 1. Clones with the KpnI/Asp718 site and restriction patterns characteristic of the trp promoter are chosen and are called pTrpl. The sequence downstream from the trp promoter in pTrpl is verified by sequencing.

B) Construction of a Truncated BSt Gene

To delete the 5'-untranslated region, the presequence, and the sequence coding for the beginning of BSt, the 494 bp PvuII fragment 3 is isolated from pLG23 (Chart 2). pLG23 was deposited in accordance with the Budapest Treaty on May 12, 1981 with the Northern Regional Research Laboratory in Peoria, Ill., USA and assigned Accession Number NRRL B12436. pLG23 contains the full length cDNA for BSt, including the 5' and 3' untranslated regions, cloned into the PstI site of pBR322. The host microorganism is *E. coli* HB101. The characteristics of this plasmid have been fully described in European patent application 67026 published on Dec. 15, 1982 and in U.S. patent application, Ser. No. 269,187, filed Jun. 1, 1981, both of which are incorporated herein by reference. Fragment 3 contains the cDNA sequence coding for amino acid residues 24 to 188 of BSt (see Table 1). Fragment 3 is then ligated to pTrpl previously digested with KpnI and treated with Klenow fragment to remove the sticky ends (fragment 4). Ligation of the BSt fragment to the vector in the desired orientation produces a BSt cDNA sequence missing the codons for the first 22 amino acid residues. The desired clone, selected by the characteristic restriction patterns and confirmed by DNA sequencing, is named pTrp-BStml.

The BSt cDNA contains 2 PvuII sites, one at the codon for amino acid residue 23 and one at residue 188. For ease of manipulation of the truncated BSt sequence, the second PvuII site is removed in pTrp-BStml. To remove this PvuII without changing the amino acid residues, the 56 bp region between MstII and BamHI in pTrp-BStml is replaced with oligonucleotides. In chart 3, the large BamHI/MstII fragment 5 is isolated from pTrp-BStml and ligated to 4 oligonucleotides assembled and isolated to produce fragment 6. The resulting plasmid, called pTrp-BStmlb, is selected by characteristic restriction patterns and verified by DNA sequencing. In pTrp-BStmlb, the BSt sequence is truncated as in pTrp-BStml, i.e., missing the codons for the first 22 amino acids. The sequence at the 3'-end after the MstII site is modified to remove the PvuII site and to introduce a HindIII site, without changing the amino acid sequence. Two stop codons followed by a BamHI site are introduced immediately at the end of the gene.

C) Construction of plasmids for BSt expression

To obtain high level expression of mature BSt, four oligonucleotides are used to replace the small ClaI to PvuII region in Trp-BStmlb to supply the missing BSt sequence. Due to the presence of another PvuII site in the vector, it is simpler to separate the vector into two portions. As shown in Chart 4, the 4.3 kb MstII/ClaI fragment 7 is isolated from pTrp-BStmlb. This fragment contains the trp promoter/operator, trpL Shine-Dalgarno sequence, pBR322 replication origin, ampicillin resistance determinant, and the 3'-end of the BSt gene. The 450 bp PvuII/MstII fragment 8 containing the sequence coding for BSt amino acid residues 24 to 176 is also isolated from pTrp-Bstmlb. Fragments 7 and 8 are ligated to fragment 9, the block of 4 oligonucleotides already assembled and purified. The resulting plasmid, selected by colony hybridization using one of the 4 oligonucletides as a probe and confirmed by DNA sequencing, is called pTrp-BStm4. In pTrp-BStm4, the only change made at the beginning of the BSt gene is changing the codon for alanine at position 4 from GCC to GCT.

To construct plasmids for expressing BSt with other changes at the beginning of the gene, other oligonucleotides assembled as 4 in a block are used to ligate to fragments 7 and 8. In Table 2, the oligonucleotide blocks used and the resulting plasmids are listed. The changes made are indicated by the asterisked nucleotide and listed below. The relative ability of these constructs to express BSt in *E. coli* K12 is as follows:

| Plasmid | BSt Expression % of Total Protein |
|---|---|
| pTrp—BSt102, no changes at the beginning of BSt. | <0.01% |
| pTrp—BStm4, ala 4 changed from GCC to GCT | 1% |
| pTrp—BStm5, ala 1 and ala 4 changed from GCC to GCT. | 1% |
| pMBSt4, ala 1 changed from GCC to thr (ACC). | 1% |
| pMBSt12, ala 4 changed from GCC to val (GTC). | 1% |
| pTrp—BSt[phe], ala 1 is changed to phe (TTC). | 2-5% |
| pTrp—BSt[lys], ala 1 is changed to lys (AAA). | 2-5% |
| pTrp—BStm3, ala 1 is deleted. | 15 |

EXAMPLE 2

Inductions With The cDNA Derived Genes 102, m4 and m5 in a Runaway Vector

A) Construction of Runaway Vectors p50-102, p50-BStm4 and p50-BStm5

The enhanced expression mutations of the BSt gene constructed according to Example 1 can also be used in plasmids having a runaway replicon. The vector source for the runaway replicon is designated pBEU-50 and is commerically available from A/S Alfred Benzon of DK-1700 Copenhagen, Denmark. This vector is about 10 kb in size and carries the temperature sensitive copB promoter and a down-promoter for copA. The vector also carries the resistance genes to tetracycline (tet) and ampicillin (amp).

As shown in Chart 5, plasmid DNA of pBEU-50 was digested with EcoRI and BamHI endonucleases, which each cut the vector DNA once. The digestion produces a 0.375 kb and a 10 kb fragment. The 10 kb fragment was isolated from an agarose gel by electroeluting (fragment 10).

The EcoRI/BamHI fragments containing the rBSt gene were isolated from pTrp-BSt102, pTrp-BStm4 and pTrp-BStm5 by digesting with EcoRI and BamHI. This digestion generates a 3.9 kb and a 0.872 kb fragment. The 0.872 kb fragment (fragment 11) was isolated from an agarose gel as described above. Fragment 11 contains approximately 240 bp encoding the tryptophan promoter and tryptophan leader ribosomal binding site. The remainder of the fragment encodes the rBSt cDNA gene.

The three rBSt cDNA fragments (exemplified by fragment 11 in Chart 5) were each cloned by ligating the fragments with fragment 10 isolated from pBEU-50. The plasmids so produced were transformed into competent E. coli cells (Maniatis). Replacement of the original EcoRI/BamHI fragment with the rBSt fragment functionally destroys the tetracycline resistance gene. Colonies from the transformation were screened for tetracycline sensitivity and DNA from selected colonies was analyzed by restriction digestions to confirm the construction. The resultant vectors were referred to as p50-102, p50-BStm4 and p50-BStm5. p50-102 containing no modifications in the beginning of BSt was constructed to compare with p50-BStm4 and p50-BStm5 where the BSt was modified at the codons for ala4 (p50-BStm4) and ala1 and ala4 (p50-BStm5). By using the same method, the other novel cDNAs from Example 1 can be used to construct similar plasmids designated p50-MBSt4, p50-MBSt12, p50-BSt[phe], p50-BSt[lys], and p50-BStm3.

B) Construction of Dual Replicon Runaway Vectors

The following example provides details on the construction of a novel combination of replicons useful for the expression of the somatotropins described herein. This class of chimeric vectors are designated pURA. The first step in the construction involves the isolation of the runaway replicon and associated genes from the Benzon family of plasmids (see Chart 6). A 2.4 kb AhaII-NdeI fragment (fragment 12) was isolated from a pBEU-50-related Benzon vector called pBEU-17 (13.8 kb) which is commercially available from A/S Alfred Benzon. Fragment 12 (3.6 kb) contains the entire replication region of the vector and was cloned into the NarI and NdeI sites of pBR322. The cloning replaces about 2 kb of pBR322 with the 2.4 kb from pBEU-17. The AhaII and NarI restriction sites share complementary ends and a NarI site is regenerated. The NdeI site is also regenerated. The vector contains a double origin of replication, one from pBEU-17 and one from the pBR322 vector. The resultant vector is designated pURA (5 kb). This vector also contains the unique restriction sites for EcoRI and BamHI which were present in the original pBR322 plasmid.

To express a somatotropin using the chimeric plasmids of the pURA series, for example, the BSt encoded by pTrp-BStm4 from Example 1 (the m4 gene), the expression vector pURA-m4 was constructed from a triple ligation (Chart 7). Ligated were: (1) an isolated EcoRIBamHI fragment (875 bp) from p50-BStm4 (Chart 5) which contains the trp promoter, the trp leader ribosomal binding site, and the m4 gene (fragment 13); (2) a transcription terminator for the E. coli genes rpoBC that was isolated as a 350 bp BamHI fragment (fragment 14) from the plasmid vector pVV202T (obtained from Dr. Charles Yanofsky, Stanford Medical School); and, (3) a pURA plasmid vector fragment (4.6 kb, fragment 15) that was isolated after pURA was digested with EcoRI and BamHI. Fragments 13-15 were mixed, ligated and transformed into competent E. coli cells. Vector DNA from the transformed clones was analyzed, and a vector that had the terminator in the same orientation with respect to the transcription of the m4 gene as it is to the rpoBC genes in the E. coli chromosome was designated pURA-m4 (5.8 kb). A schematic of pURA-m4 is presented in Chart 7.

It should be noted that the particular transcription terminator chosen is not the only terminator useful in this invention. Any of a number of efficient rho independent transcription terminators could be substituted. For a review of these terminators see Cell, 32:1029–1032 (1983) and Ann. Rev. Genet., 13:319–53 (1979).

In a like fashion the BSt genes from pTrp-BStm5, p50-MBSt4, p50-MBSt12, p50-BSt[phe], p50-BSt[lys], and p50-BStm3 can be inserted into pURA to obtain pURA-m5 pURA-MBSt4, pURA-MBSt12, pURA-BSt[phe], pURA-BSt[lys], and pURA-BStm3.

C) Construction of an E. coli Host for rBSt Expression

The E. coli progenitor strain was obtained from the American Type Culture Collection and is designated ATCC e23716. This strain is lysogenic for the bacteriophage lambda and also harbors the F plasmid (Bachmann, B. J., Bact. Rev. 36:525–557 (1972)).

The lambda lysogen was removed from the strain. This was accomplished by the P1vir bacteriophage transduction technique as described by Miller, J. H. in Experiments in Molecular Genetics, Cold Spring Harbor Laboratory (1972). The P1vir bacteriophage is available as a part of the "Experiments with Gene Fusion Strain Kit" from the Cold Spring Harbor Laboratories, Cold Spring Harbor, N.Y.

Bacteriophage P1vir was grown up on E. coli strain CGSC 6180 which is available from the Coli Genetic Stock Center, c/o Dr. Barbara Bachmann, Yale University, New Haven, Ct. 06510. This strain is not lysogenic for the bacteriophage lambda, and contains a Tn10 element inserted into the nadA gene (which encodes the A protein of the quinolinate synthetase) and is located adjacent to the integration site of the bacteriophage lambda. The Tn10 element destroys the nadA gene and causes the cell to be dependent on an exogenous source of nicotinamide. The Tn10 element carries a gene which codes for resistance to tetracycline. The P1vir lysate from CGSC 6180 (nadA::Tn10) was used to transduce the nadA::Tn10 allele into the ATCC e23716 by selecting for resistance to tetracycline. A number of colonies from the selection were tested for recombinational loss of the adjacent lambda phage by sensitivity to bacteriophage T4rII (Benzer, S., Proc. Natl. Acad. Sci. USA, 47:403–408 (1961)). The nadA::Tn10 allele was removed by growing P1vir on W3110 strain (available from the Coli Genetic Stock Center, New Haven, Ct. which has the normal nadA gene and is not lysogenic for lambda. Selection for the normal nadA allele was performed by plating the cells on a medium that was not supplemented with nicotinamide.

Next the F plasmid was removed by growing cells in the presence of 4 $\mu$g/ml rifampicin for multiple generations. Cells that had lost the F plasmid were identified by their inability to support the growth of the F plasmid-specific bacteriophages (Caro, L. G. and M. Schnos, Proc. Natl. Acad. Sci. USA, 56:126–131 (1966)). The resultant strain was designated K12D.

C) Induction of the p50-102, p50-BStm4 and p50-BStm5 Vectors in the K12D Strain

The vectors were transformed into competent K12D cells by selecting for ampicillin resistance. The three cultures were grown overnight in LB media containing 100 $\mu$g/ml ampicillin. The following day the cells were subcultured 1/50 into the same media, and incubated at 27° C. using a sterile flask in a New Brunswick shaking incubator set at about 275 rpm. The cultures were grown to an O.D.$_{550nm}$ of 0.2 to 0.3., and then shifted to 38.5° C. to induce runaway replication.

Samples were taken after the inductions and were analyzed by SDS-PAGE gel analysis (Laemmli, supra). The gels were stained with Coomassie Blue and were scanned to determine the amount of visible rBSt.

There was no detectable rBSt for the inductions of p50-102. The cultures containing either p50-BStm4 or p50-BStm5 produced between 13 to 18 area percent BSt.

A comparison with HPLC was made between the amount of rBSt present in a 20 O.D. sample of induced cells containing p50-102 and p50-BStm4. The p50-102 showed no detectable rBSt (0.00 mg/ml), and the p50-BStm4 showed 179.02 mg/ml.

These results show that the single base change in the codon for the alanine at the fourth position of BSt from GCC to GCT causes high level rBSt production in the runaway plasmids.

EXAMPLE 3

Construction of E. coli Hosts with the rpoH112 and hflB29 Alleles

The E. coli strain CAG671 was obtained from Dr. Carol Gross (University of Wisconsin, Madison, Wis.). This strain contains the rpoH112 allele and has an adjacent insertion zhg: : Tn10 (Grossman, A. D., et al., J. Bact., 161:939-943 (1985)). The rpoH112 allele was introduced into the K12D strain by growing the bacteriophage P1vir on the CAG671 strain and using the lysate to transduce the K12D strain to tetracycline resistance (encoded in the Tn10 located adjacent to the rpoH112 allele) and to co-transduce in the rpoH112 allele (Miller, J. H., supra). The resultant strain was designated D112 and was deposited in accordance with the Budapest Treaty on Feb. 4, 1987, with the Agricultural Research Service Culture Collection, Northern Regional Research Center, 1815 North University Street, Peoria, Ill. 61604, USA and assigned Accession Number NRRL B-18168.

The E. coli strain x9393 was obtained from Dr. Ronald Sommerville (Purdue University, Indiana). This strain contains the hflB29 allele, and an adjacent Tn10 element (Banuett, F. et al., J. Mol. Biol., 187:213-224 (1986)). The hflB29 allele was introduced into the K12D strain by the same procedure that was described for rpoH. The resultant strain was designated B29.

EXAMPLE 4

Expression of BST Using E. coli Hosts with the rpoH112 and hflB29 Alleles and Dual Replicon Plasmids The vector pURA-m4 was transformed into competent cells of E. coli strains K12D, D112 (K12D with rpoH112) and B29 (K12D with hflB29). Cultures were grown in shaker flasks containing LB broth in a 27° C. air shaker. At the desired time the cultures were shifted to a 37° C. shaker to induce runaway vector replication and rBST expression. Samples were taken prior to the heat shift and at various times thereafter. The samples were analyzed by SDS-PAGE and gel scanning. The results show that rBSt reached 13.3% of visible protein in K12D, 32% in B29, and 41% in D112.

These results show that expression of rBSt is enhanced by different combinations of runaway plasmids when the disclosed modifications in the native cDNA are made but that there is a particularly advantageous elevation in expression levels when the chimeric plasmid is placed in an E. coli strain containing a rpoH or hflB allele.

EXAMPLE 5

Spontaneous Induction of Runaway Plasmid Replication and rBSt Synthesis with pURA-m4.

A) Relationship Between Spontaneous Induction of rBSt Synthesis and Spontaneous Induction of Plasmid Runaway Replication Cultures of strain D112 containing the runaway replication vector pURA-m4 and adapted for fermentation (called BST-1, see section C below) were inoculated into flasks of defined inorganic salts media supplemented with glucose and either yeast extract or casamino acids. From shake flasks incubated at 28° C. and shifted to 37° C. at an O.D. of 1 A$_{550}$, samples were obtained and subjected to SDS-PAGE (Laemmli, supra). Such samples shows appreciable rBSt synthesis, due to the thermal inducibility of plasmid runaway replication and rBSt expression characteristic of pURA-m4. However, when samples obtained from companion flasks containing the same media and inoculated with the same culture, but incubated at 28° C. throughout, were subjected to SDS-PAGE analyses, appreciable rBSt synthesis was also observed. These observations shown that strain BST-1 can spontaneously (i.e., non-thermally) induce rBSt synthesis.

Fermentations done in defined inorganic salts media supplemented with glucose and yeast extract confirmed the ability of pURA-m4 to undergo spontaneous induction of rBSt synthesis. Furthermore, these fermentations established that the spontaneous induction of rBSt synthesis occurred at the same time as spontaneous induction of plasmid runaway replication occurred. In the absence of thermal induction, pURA-m4 spontaneously increased to substantially higher copy numbers. The data in Table 3 depict the relationship between the spontaneous induction of plasmid copy number and spontaneous induction of rBSt synthesis. By approximately 15 hours post-inoculation, rBSt accumulation was detected in samples subjected to reversed-phase HPLC analysis. A similar temporal increase in plasmid copy number (plasmid DNA content) was observed for pURA-m4 during fermentations conducted at 28° C. throughout.

B) Spontaneous Inducibility of Plasmid Runaway Replication in the Absence of rBSt Synthesis Plasmid pURA4 Δbgh$_{E/H}$ was constructed from plasmid pURA-m4 by removal of an approximately 850 base pair fragment bounded by EcoRI and HindIII restrictions sites, thus deleting the gene encoding rBSt synthesis (Chart 13).

Plasmid pURA4 Δbgh$_{E/H}$ was introduced into E. coli strain BST-1C, a plasmid-free derivative of strain BST-1 obtained following growth on defined minimal medium at 42° C. and found cured of pURA-m4, by DNA-mediated transformation. The resulting strain was unable to synthesize rBSt. E. coli host strain BST-1C was deposited in accordance with the Budapest Treaty on Feb. 2, 1988, with the Agricultural Research Service Culture Collection, Northern Regional Research Center, 1815 North University Street, Peoria, Ill. 61604, U.S.A. and assigned Accession Number NRRL B-18303.

Data from fermentations that were conducted in defined inorganic salts media supplemented with glucose and yeast extract shown the ability of strain BST-1C (pURA4 Δbgh$_{E/H}$) to undergo spontaneous induction of runaway plasmid replication. When compared with plasmid-containing preparations obtained from strain BST-1, preparations from BST-1C (pURA4 Δbgh$_{E/H}$) established that plasmids from both strains had spontaneously increased to levels which were very similar by the ends of their respective fermentations (Table 4). Therefore, spontaneous induction of runaway replication to a substantially higher plasmid copy number was independent of host rBSt synthesis per se.

C) Fermentation Conditions for Spontaneous Induction

Set forth here is the preferred fermentation protocol for the *E. coli* hosts transformed with pURA plasmids.

The strain construction used in these experiments was designated BST-1. BST-1 was derived by adapting the D112 strain transformed with pURA-M4 to the fermentation seed medium set forth below. BST-1 can also be produced by transforming strain BST-1C (above) with p-URA-m4 (above).

Two fermentation media, RB6 and RB7, were used in the experiments. The composition of these media and methods of preparation are as follows:

A) Medium Preparation Procedures:
1) Medium RB6:

| Ingredient | Concentration | Amount |
| --- | --- | --- |
| Na(NH$_4$)HPO$_4$.H$_2$O | 11 g/l | 99 g |
| K$_2$HPO$_4$ | 2.6 g/l | 24 g |
| Citric Acid.H$_2$O | 2.1 g/l | 19 g |
| Yeast Extract | 1.0 g/l | 9.0 g |
| (NH$_4$)$_2$SO$_4$ | 0.66 g/l | 5.9 g |
| MgSO$_4$ | 0.25 g/l | 2.2 g |
| SAG 4130 | 0.75 ml/l | 6.8 ml |

Q.S. the above ingredients to 8.3 l with R.O. water in a 16 l fermentor, sterilize at 121° C. for 20 minutes and then cool. Prior to inoculating the fermentor, aseptically add 675 ml of a sterile 500 g/l glucose solution, 9 ml of sterile micronutrients and 9 ml of a sterile 25 g/l ampicillin solution to the fermentor (See "Fermentation Additions" section below).

2) Medium RB7:

| Ingredient | Concentration | Amount |
| --- | --- | --- |
| Na(NH$_4$)HPO$_4$.H$_2$O | 11 g/l | 99 g |
| K$_2$HPO$_4$ | 2.6 g/l | 24 g |
| Citric Acid.H$_2$O | 2.1 g/l | 19 g |
| Yeast Extract | 1.0 g/l | 9.0 g |
| D,L-Methionine (food grade) | 0.75 g/l | 6.7 g |
| (NH$_4$)$_2$SO$_4$ | 0.66 g/l | 5.9 g |
| MgSO$_4$ | 0.25 g/l | 2.2 g |
| SAG 4130 | 0.75 ml/l | 6.8 ml |

The remainder of the procedure is the same as that given for RB6.

3) Fermentation Additions:
a) Micronutrient Solution (200 ml):

| Ingredient | Amount (grams) |
| --- | --- |
| FeSO$_4$.H$_2$O | 5.22 |
| Citric acid.H$_2$O | 5.04 |

Add 8 ml of trace components* to the above ingredients, q.s. to 200 ml, and sterilize by passage through a 0.22 micron filter.

(*) The trace component solution is prepared as follows:

| Ingredient | Amount (mg) |
| --- | --- |
| Citric acid.H$_2$O | 7000 |
| H$_3$BO$_4$ | 247.4 |
| MnCl$_2$.4H$_2$O | 158.0 |
| CoCl$_2$.6H$_2$O | 71.4 |
| (NH$_4$)$_6$Mo$_7$O$_{24}$.4H$_2$O | 37.1 |
| ZnSO$_4$.7H$_2$O | 28.8 |
| CuSO$_4$ | 15.9 |

Q.S. to 100 ml with distilled water.

b) 500 g/liter glucose addition (675 ml):

Q.S. 338 g of glucose in a 1/liter shake flask to 675 ml with R.O. water, add sufficient 1N H$_2$SO$_4$ to decrease the pH to 4, and sterilize at 121° C. for 20 minutes.

c) 25 g/l ampicillin addition (300 ml):

Prepare a 25 g/l ampicillin solution by dissolving 9 g of ampicillin into 360 ml of R.O. water. Titrate the suspension to pH 8.0 by adding 1N NaOH in a dropwise manner. Sterilize the resulting solution using a 0.45 micron filter, refrigerate, and use within 24 hours.

A 16-liter fermentor containing 9 liters of medium RB6 or RB7 (post-sterilization) was inoculated with the 30 ml of broth from a shake flask. The procedures for storing the culture and for preparing the seed culture are as follows:

B) Ampoule and Seed Preparation Procedures
1) Prepare Petri dishes using the following medium:

| Ingredient | Concentration | Amount |
| --- | --- | --- |
| Bacto-agar | 15 g/l | 3.75 g |
| Trypticase soy-agar | 40 g/l | 10.0 g |

Q.S. the above ingredients to 250 ml with R.O. water, sterilize the resulting solution in a 500 ml Erlenmeyer flask sealed with a cotton plug at 121° C. for 20 minutes, and then place the flask in a 50° C. water bath. Transfer the culture medium from the heated flask into presterilized Petri dishes. Allow the dishes to dry overnight under a laminar flow hood with the dish covers propped open. Store the covered dishes in the inverted position.

2) Prepare single colonies of recombinant *E. coli* by streaking the above prepared Petri dishes with the contents of a single ampule of *E. coli* that was stored under the gaseous phase of liquid nitrogen. Incubate the Petri dishes at 28° C. for 2 days.

3) Prepare 3 shake flasks containing the following medium:

| Ingredient | Concentration | Amount |
| --- | --- | --- |
| K$_2$HPO$_4$ | 2.6 g/l | 0.078 g |
| Na(NH$_4$)HPO$_4$.4H$_2$O | 11.0 g/l | 0.33 g |
| Citric Acid.H$_2$O | 2.1 g/l | 0.063 g |
| (NH$_4$)$_2$SO$_4$ | 0.66 g/l | 0.020 g |
| MgSO$_4$.7H$_2$O | 0.99 g/l | 0.030 g |
| Glycerol | 5.0 g/l | 0.15 g |
| Yeast Extract | 10.0 g/l | 0.30 g |
| R.O. Water | | 29.0 ml |

Seal the above shake flasks with cotton plugs, sterilize them at 121° C. for 20 minutes, and then allow them to cool to room temperature before use.

4) Inoculate each of the above flasks by aseptically transferring a single colony to it. Place the shake flasks in a controlled environment incubator shaker set to 320 rpm and 28° C. Sample one of the shake flasks periodically and determine the absorbance at 550 nm of one ml of sample diluted with 9 ml of 1% formaldehyde. When an absorbance of 0.3 is attained, refrigerate the remaining two shake flasks and use one of these flasks as a fermentation seed within 24 hours after refrigeration.

5) Prepare 6 shake flasks containing the following medium:

| Ingredient | Concentration | Amount |
| --- | --- | --- |
| $K_2HPO_4$ | 2.6 g/l | 0.052 g |
| $Na(NH_4)HPO_4.4H_2O$ | 11.0 g/l | 2.2 g |
| Citric Acid.$H_2O$ | 2.1 g/l | 0.42 g |
| $(NH_4)_2SO_4$ | 0.66 g/l | 0.14 g |
| $MgSO_4.7H_2O$ | 0.99 g/l | 0.20 g |
| Glycerol | 5.0 g/l | 1.0 g |
| Yeast Extract | 10.0 g/l | 2.0 g |
| R.O. Water | | 298.0 ml |

Seal the above shake flasks with cotton plugs, sterilize them at 121° C. for 20 minutes, and allow them to cool to room temperature before use.

6) Prepare a 25 g/l ampicillin solution by dissolving 9 grams of ampicillin into 360 ml of R.O. water. To completely dissolve the ampicillin, titrate the suspension to pH 8.0 by adding 1N NaOH in a dropwise manner. Sterilize the solution using a 0.45μ filter and refrigerate. Use the solution within 24 hours.

7) Inoculate the above shake flasks by aseptically adding 1 ml of seed and 0.3 ml of the ampicillin solution to each shake flask. Place the shake flasks in a controlled environment incubator shaker set to 320 rpm and 28° C. Sample one of the shake flasks periodically and determine the absorbance of one ml of sample diluted with 9 ml of 1% formaldehyde at 550 nm. When an absorbance of 0.1 is attained, refrigerate the remaining shake flasks.

8) Add 67 g of glycerol to each shake flask prior to filling ampoules.

9) When using a fixed delivery pump to fill ampoules, set the delivery volume to 1 ml. Ice and occasionally stir the culture while filling the ampoules. (The ampoules must be chilled prior to filling).

The pH of the fermentation broth is controlled using ammonium hydroxide (50 wt %) on/off pH control. The agitation and aeration rates are set to 600 rpm and 13.5 slm, respectively, and the backpresure, pH, and temperature in the fermentor are controlled at 10 psig, 7.2° and 27° C., respectively.

BST-1 was grown on medium RB6 at the 9 liter scale at 27° C. Dark polar inclusion bodies were formed after spontaneous induction at a cell density of 0.5 g/l (dry wt.) was exceeded. BSt and cell yields of 1.59 g/l and 5.1 g/l, respectively, were obtained after 32 hours of fermentation.

EXAMPLE 6

Plasmid Maintenance Stability with pURA-m4

A) Stability of pURA-m4 in BST-1 Shake-Flask Cultures

The maintenance stability of pURA-m4 in strain BST-1 was quantitated during experiments conducted with cultures grown at 28° C. for several generations in complex liquid medium without ampicillin. Aliquots were successively obtained from cultures and subcultured at a $10^{-5}$th dilution into flasks containing fresh complex medium without ampicillin. Following incubation at 28° C., the process was repeated. At the beginning and end of each passage cycle, culture samples were obtained, diluted, and plated on plates on complex medium, either unsupplemented or supplemented with 40 μg/ml ampicillin, and incubated at 28° C. Quantitation of the total viable population (without ampicillin) allowed estimation of the total number of generations (n) that transpired during each passage cycle, according to the following:

$n = (lnX - lnX_o)/ln2$

Comparisons of the viable populations quantitated on both media allowed estimation of the plasmid stability frequency (PSF), according to the following:

PSF=(CFU/ml on Ap plates)/(CFU/ml on unsupplemented plates)

The data showed that plasmid pURA-m4 remained stable throughout an extended period of growth and up to 131.9 generations, as ≧95% of the bacteria were detected as being ampicillin-resistant.

B) Stability of pURA-m4 in Fermentor Cultures of BST-1

The stability of pURA-m4 in strain BST-1 was quantitated during fermentations at the 5000-liter scale in media without ampicillin. Sample aliquots were aseptically obtained at different times during the course of fermentations and handled as described above (Example 6, A) to estimate the number of bacterial generations that had transpired and the plasmid stability frequency. The data showed that pURA-m4 was completely stable throughout the 18.4 generations of the fermentation.

EXAMPLE 7

Expression of Porcine Somatotropin (PSt)

A) Construction of Expression Vector pTrp-conSD

Referring now to Chart 8, to make pTrp-conSD, oligonucleotides are used to replace the HpaI-HindIII region in pSK4, as shown in Chart 8. pSK4 is treated with HindIII, bacterial alkaline phosphatase (BAP) and HpaI to produce fragment 16. Fragment 17 is produced synthetically and is a double-stranded DNA sequence containing four oligonucleotides which are assembled and then purified. Fragments 16 and 17 are ligated together and cloned. Clones with restriction patterns characteristic of the Trp promoter are chosen and are designated pTrp-conSD. The sequence downstream of the Trp promoter in pTrp-conSD is verified by sequencing. Expression vector pTrp-conSD contains the promoter and operator region of the tryptophan operon, and an E. coli consensus Shine-Dalgarno (conSD, GGAGG) sequence in a pBR322 background with ampicillin resistance.

B) Construction of a Plasmid Containing PSt

Referring now to Chart 9, the method for preparation of the cDNA for PSt is known (P. H. Seeburg et al., DNA 2:37-45, 1983; and European Patent application, 111,389, U.S. Ser. No. 439,977). The cDNA is cloned into the PstI site of pBR322 by GC tailing. The fulllength cDNA for PSt including the 5' and 3' untranslated regions can be excised from the vector by PstI digestion. This PstI fragment (fragment 19, 900 bp) contains two HgiAl sites, one in the presequence and one at the 15th codon of the mature sequence. The 660 bp HgiAl - PstI fragment containing the truncated PSt cDNA sequence is cloned into the expression vector pTrp-conSD together with two oligonucleotides. As shown in Chart 9, pTrp-conSD is treated with KpnI, Klenow fragment and ClaI to produce fragment 18. Fragment 18 is then ligated to fragments 20 and 21. Fragment 20 contains the PSt cDNA truncated for the first 14 codons of the mature PSt sequence with a HgiAl sticky end at the 5'-end and blunted PstI at the 3'-end. Fragment 21 is the annealed product of two complimentary oligonucleotides which contain the first 14 codons for the mature PSt, the translation initiation codon, ATG, a ClaI sticky end for ligating into pTrp-conSD, and a HgiAl sticky end for ligating to the PSt fragment. In the resulting construct, pTrp-PStl, the expression of PSt is under the control of the Trp promoter in the pBR322 background. The codon for the fourth alanine in this PSt is changed from GCC in native cDNA to GCT.

In a similar manner, pTrp-PStc is constructed where no changes in the PSt cDNA are made.

C) Introduction of the PStl Gene Into the pURA Expression Vector

The construction of a PSt expression vector using the chimeric runaway replicon of the URA vectors and the Trp promoter in combination with a consensus Shine-Dalgarno sequence is detailed herein.

Referring to Chart 10, the pURA vector is digested with the EcoRI and BamHI restriction enzymes and fragment 22 (4.6 kb) containing the double replication ori and the ampicillin resistance gene is isolated as previously described.

The pTrp-PStl vector (Chart 9) digested with restriction enzymes EcoRI and BamHI and fragment 23 (900 bp) is isolated as previously described. Fragment 23 contains the trp promoter, the consensus ribosomal binding site and the modified porcine somatotropin gene. Fragments 22 and 23 are ligated to yield pURA-PStl (Chart 10). Plasmid pURA-PStl is then transformed into competent cells of E. coli. Confirmation of the cloning is made by restriction digestions of the clones and DNA sequencing.

This vector does not require a transcriptional terminator at the end of the porcine gene. The DNA sequence downstream of the coding region of the gene which originated from the cDNA has sufficient transcriptional termination activity in *E. coli.*

D) Induction of PSt Expression in *E. coli.*

Plasmid pURA-PStl is transformed into competent D112 cells and induced as previously described for rBSt. Procedures for the isolation of rPSt are also as described for rBSt. Expression levels have reached 25% of total cellular protein.

EXAMPLE 8

Expression of Porcine Somatotropin (PSt) with the TrpL Shine-Delgarno Sequence A) Construction of Expression Vectors pTrp-trpL-PStc and pTrp-trpL-PStl To further evaluate the expression levels of the porcine gene constructions PStc and PStl , these genes were placed under control of the Trp promoter and the trpL Shine-Delgarno sequence.

Referring to Chart 11, expression vector pTrpl (Example 1) was used as the source of the Trp promoter and the TrpL Shine-Delgarno sequence. pTrpl is first digested with KpnI and treated with Klenow fragment to generate a blunt end. The DNA is then cut with ClaI and the large vector fragment (fragment 24) is purified as described above. A PstI digestion of the cDNA clone of the PSt gene (Example 5) is treated with Klenow fragment to generate a blunt end and is then cut with HgiA1. This fragment (fragment 20) is then purified. A synthetic double-stranded DNA linker fragment is constructed from two DNA oligonucleotides. Two synthetic linker fragments are made. The first contains the change from GCC to GCT for the second alanine codon of PSt (fragment 25) and the second linker contains unmodified PSt cDNA sequence (fragment 26). The fragments 20, 24 and 25 are ligated to produce pTrp-trpL-PSt1, and the fragments 20, 24 and 26 are ligated to produce pTrp-trpL-PStc.

B) Construction of pURA Vectors Which Contain Either the trpL-PStc or the trpL-PStl Gene The construction of PSt expression vectors using the chimeric runaway replicon of the pURA vectors and the trp promoter in combination with the trp leader Shine-Delgarno sequence (trpL) is detailed herein (Chart 12).

The pURA vector is digested with EcoRI and BamHI restriction enzymes and fragment 22 (4.6 kb) is isolated. The pTrp-trpL-PStc and pTrp-trpL-PStl vectors (Chart 11) are digested with restriction enzymes EcoRI and BamHI and a fragment of approximately 900 bp is isolated from each digestion. The fragments so produced from pTrp-trpL-PStc and from pTrp-trpL-PStl are designated fragments 27 and 28, respectively. Fragments 22 and 27 are ligated to form pURA-trpL-PStc. Fragments 22 and 28 are ligated to form pURA-trpL-PStl . Confirmation of the clonings is made by restriction analysis and DNA sequencing.

C) Induction of pURA-trpL-PStc and pURA-trpL-PStl

Plasmids pURA-trpL-PStc and pURA-trpL-PStl are transformed into competent cells of strain D112 and induced as previously described for rBSt. Samples of the inductions are analyzed by SDS-PAGE, Coomassie Blue staining, and gel scanning. Porcine somatotropin was not detectable with the pURA-trpL-PStc induction. The induction of pURA-trpL-PStl showed porcine somatotropin being expressed at a level of about 5% of the total visible protein.

EXAMPLE 9

Expression of Human Interleukin-1$\beta$ (IL-1$\beta$)

A) Construction of a Plasmid Containing the IL-1$\beta$ Gene

The cloning of the human IL-1$\beta$ sequence originated from a cDNA sequence containing part of the 5' untranslated region and all of the coding region of IL-1$\beta$ and ending after the stop codon. This cDNA sequence was constructed from a human SK-Hep-1 cell line and cloned into pTrpl (Chart 1) to yield pTrp-ILl -1. Another subcloning was done to construct pTrp-conSD-HC-ILl -1, containing the mature IL-1$\beta$ sequence. The construction of these plasmids has been published (D. B. Carter, et al., 1988, Proteins: Structure, Function and Genetics, in press, which is incorporated herein by reference). Plasmid pTrp-conSD-HC-ILl -1 is shown in Chart 14.

Plasmid pTrp-conSD-HC-ILl -1 was digested with EcoRI and BamHI and the resulting 790 base-pair fragment was isolated and then mixed and ligated with the 4.6 kilobase-pair EcoRI/BamHI fragment of pURA (Chart 6) to produce pURA-IL-1-1A. pURA-IL-1-1A was subsequently digested with BamHI and mixed and ligated with the BamHI fragment 14 (Chart 7) of pVV202T to yielded pURA-IL1-1C.

B) Spontaneous Induction of IL-1β Expression

The vector pURA-IL1-1C was transformed into competent cells of BST-1C. Seed cultures of BST-1C (pURA-IL1-1C) were grown in shake flasks containing defined inorganic salts medium supplemented with glucose, yeast extract, and tryptophan, and incubated at 28° C. throughout. Culture aliquots were subcultured into defined inorganic salts medium supplemented with glucose and casamino acids, and the cultures were then incubated at 28° C. throughout. Culture samples were periodically withdrawn and subjected to SDS-PAGE analyses, followed by densitometric scanning of the gels, to quantitate the level of IL-1β produced. The data in Table 5 show that IL-1β production was spontaneously induced under such conditions, and that such spontaneous induction resulted in a level of IL-1β which was very similar to that which was attained by the same culture in identical medium, but which was shifted from 28° C. to 37° C. at a culture O.D. 1 $A_{550}$ (thermally induced).

TABLE 1

Bovine somatotropin - cDNA sequence and corresponding amino acid sequence.

```
                30                                                  60
GCC TTC CCA GCC ATG TCC TTG TCC GGC CTG TTT GCG AAC GCT GTG CTC CGG GCT CAG CAC
Ala Phe Pro Ala Met Ser Leu Ser Gly Leu Phe Ala Asn Ala Val Leu Arg Ala Gln His 90                                                 120
CTG CAT CAG CTG GCT GCT GAC ACC TTC AAA GAG TTT GAG CGC ACC TAC ATC CCG GAG GGA
Leu His Gln Leu Ala Ala Asp Thr Phe Lys Glu Phe Glu Arg Thr Tyr Ile Pro Glu Gly 150                                                 180
CAG AGA TAC TCC ATC CAG AAC ACC CAG GTT GCC TTC TGC TTC TCT GAA ACC ATC CCG GCC
Gln Arg Tyr Ser Ile Gln Asn Thr Gln Val Ala Phe Cys Phe Ser Glu Thr Ile Pro Ala 210                                                 240
CCC ACG GGC AAG AAT GAG GCC CAG CAG AAA TCA GAC TTG GAG CTG CTT CGC ATC TCA CTG
Pro Thr Gly Lys Asn Glu Ala Gln Gln Lys Ser Asp Leu Glu Leu Leu Arg Ile Ser Leu 270                                                 300
CTC CTC ATC CAG TCG TGG CTT GGG CCC CTG CAG TTC CTC AGC AGA GTC TTC ACC AAC AGC
Leu Leu Ile Gln Ser Trp Leu Gly Pro Leu Gln Phe Leu Ser Arg Val Phe Thr Asn Ser 330                                                 360
TTG GTG TTT GGC ACC TCG GAC CGT GTC TAT GAG AAG CTG AAG GAC CTG GAG GAA GGC ATC
Leu Val Phe Gly Thr Ser Asp Arg Val Tyr Glu Lys Leu Lys Asp Leu Glu Glu Gly Ile 390                                                 420
CTG GCC CTG ATG CGG GAG CTG GAA GAT GGC ACC CCC CGG GCT GGG CAG ATC CTC AAG CAG
Leu Ala Leu Met Arg Glu Leu Glu Asp Gly Thr Pro Arg Ala Gly Gln Ile Leu Lys Gln 450                                                 480
ACC TAT GAC AAA TTT GAC ACA AAC ATG CGC AGT GAC GAC GCG CTG CTC AAG AAC TAC GGT
Thr Tyr Asp Lys Phe Asp Thr Asn Met Arg Ser Asp Asp Ala Leu Leu Lys Asn Tyr Gly 510                                                 540
CTG CTC TCC TGC TTC CGG AAG GAC CTG CAT AAG ACG GAG ACG TAC CTG AGG GTC ATG AAG
Leu Leu Ser Cys Phe Arg Lys Asp Leu His Lys Thr Glu Thr Tyr Leu Arg Val Met Lys

570
TGC CGC CGC TTC GGG GAG GCC AGC TGT GCC TTC TAG
Cys Arg Arg Phe Gly Glu Ala Ser Cys Lal Phe End
```

TABLE 2

Synthetic Oligonucleotides Used to Complete the Synthetic 5' End of rBSt

Oligonucleotide 1. Native cDNA for pTrp—BSt102

```
    1
CGATAATG GCC TTC CCA GCC ATG TCC TTG TCC GGC CTG T
   TATTAC CGG AAG GGT CGG TAC AGG AAC AGG CCG GAC AAA CGG
                                                         2

3
TTGCC AAC GCT GTG CTC CGG GCT CAG CAC CTG CAT CAG
   TTG CGA CAC GAG GCC CGA GTC GTG GAC GTA GTC
                                                4
```

Oligonucleotide 2. pTrp—BStm4

```
    1
CGATAATG GCC TTC CCA GCT ATG TCC TTG TCC GGC CTG T
   TATTAC CGG AAG GGT CGA TAC AGG AAC AGG CCG GAC AAA CGG
                                                         2
```

TABLE 2-continued
Synthetic Oligonucleotides Used to Complete the Synthetic 5' End of rBSt

```
                        3
TTGCC AAC GCT GTG CTC CGG GCT CAG CAC CTG CAT CAG
      TTG CGA CAC GAG GCC CGA GTC GTG GAC GTA GTC
                        4
```

Oligonucleotide 3. pTrp—BStm5

```
         •                •              1
CGATAATG GCT TTC CCA GCT ATG TCC TTG TCC GGC CTG T
  TATTAC CGA AAG GGT CGA TAC AGG AAC AGG CCG GAC AAA CGG
                                   2

3
TTGCC AAC GCT GTG CTC CGG GCT CAG CAC CTG CAT CAG
      TTG CGA CAC GAG GCC CGA GTC GTG GAC GTA GTC
                        4
```

Oligonucleotide 4. pMBSt4

```
          •                             1
CGATAATG ACC TTC CCA GCC ATG TCC TTG TCC GGC CTG T
  TATTAC TGG AAG GGT CGG TAC AGG AAC AGG CCG GAC AAA CGG
                                   2

3
TTGCC AAC GCT GTG CTC CGG GCT CAG CAC CTG CAT CAG
      TTG CGA CAC GAG GCC CGA GTC GTG GAC GTA GTC
                        4
```

Oligonucleotide 5. pMBSt12

```
                           •            1
CGATAATG GCC TTC CCA GTC ATG TCC TTG TCC GGC CTG T
  TATTAC CGG AAG GGT CAG TAC AGG AAC AGG CCG GAC AAA CGG
                                   2

3
TTGCC AAC GCT GTG CTC CGG GCT CAG CAC CTG CAT CAG
      TTG CGA CAC GAG GCC CGA GTC GTG GAC GTA GTC
                        4
```

Oligonucleotide 6. pTrp—BSt[lys]phe

```
         • • •                          1
CGATAATG AAA TTC CCA GCC ATG TCC TTG TCC GGC CTG T
  TATTAC TTT AAG GGT CGG TAC AGG AAC AGG CCG GAC AAA CGG
                                   2

3
TTGCC AAC GCT GTG CTC CGG GCT CAG CAC CTG CAT CAG
      TTG CGA CAC GAG GCC CGA GTC GTG GAC GTA GTC
                        4
```

Oligonucleotide 6. pTrp—BSt[phe]phe

```
         • •                            1
CGATAATG TTC TTC CCA GCC ATG TCC TTG TCC GGC CTG T
  TATTAC AAG AAG GGT CGG TAC AGG AAC AGG CCG GAC AAA CGG
                                   2

3
TTGCC AAC GCT GTG CTC CGG GCT CAG CAC CTG CAT CAG
      TTG CGA CAC GAG GCC CGA GTC GTG GAC GTA GTC
                        4
```

Oligonucleotide 7. pTrp—BStm3

```
                                        1
CGATAATG TTC CCA GCC ATG TCC TTG TCC GGC CTG T
  TATTAC AAG GGT CGG TAC AGG AAC AGG CCG GAC AAA CGG
                                   2

3
TTGCC AAC GCT GTG CTC CGG GCT CAG GAC CTG CAT CAG
      TTG CGA CAC GAG GCC CGA GTC GTG GAC GTA GTC
                        4
```

TABLE 3

Spontaneous Induction of Runaway Plasmid Replication and rBSt Synthesis

| Time Post-Inoculation (hours) | rBSt Titer (g rBSt/liter) | Relative Plasmid Content (per $10^{10}$ bacteria)[a] |
|---|---|---|
| 9.0 | 0.0000 | 182,741 |
| 16.0 | 0.0113 | 482,268 |
| 18.0 | 0.0770 | 834,673 |
| 19.0 | 0.1303 | 1,063,058 |
| 22.0 | 0.4627 | 1,145,452 |
| 25.0 | 0.7396 | 1,088,053 |
| 27.0 | 0.9543 | 1,152,051 |
| 29.0 | 1.0871 | 1,205,500 |
| 31.0 | 1.0975 | 1,122,224 |

[a]Peak area from densitometric trace of covalently-closed circular monomer plasmid band.

TABLE 4

Spontaneous Induction of Runaway Plasmid Replication in the Absence of rBSt Synthesis

| Plasmid | Time Post-Inoculation (hours) | Relative Plasmid Content (per $10^{10}$ bacteria)[a] |
|---|---|---|
| pURA—m4 | 16.0 | 591,763 |
| pURA—m4 | 22.0 | 1,249,226 |
| pURA—m4 | 31.0 | 1,149,770 |
| pURA4 $\Delta bgh_{E/H}$ | 18.0 | 540,450 |
| pURA4 $\Delta bgh_{E/H}$ | 24.0 | 970,199 |
| pURA4 $\Delta bgh_{E/H}$ | 30.0 | 1,755,525 |

[a]Peak area from densitometric trace of covalently-closed circular monomer plasmid band.

TABLE 5

Spontaneous Induction of IL—1β Production with the Runaway Vector pURA—IL1—1C

| Culture Incubation Temperature | Time Post-Inoculation (hours) | IL13 1β Produced (% total protein) |
|---|---|---|
| 28° C. | 0.0 | 3.9 |
| | 3.0 | 2.3 |
| | 10.0 | 3.5 |
| | 28.0 | 18.8 |
| 28° C. → 37° C. | 28.0 | 20.6 |

CHART 1

Construction of pTrpl (a) pSK4 is cut with ClaI and BamHI to isolate fragment 1 (4.2 kb).

Fragment 1

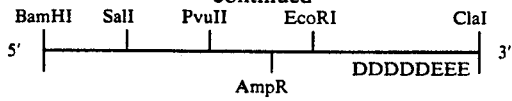

-continued (b) The synthetic sequence of double-stranded DNA, fragment 2, is ligated to fragment 1 to yield pTrpl (4.3 kb).

Fragment 2

5' CGATAATGCAGGTACCTGTGCTTTCTAATAG 3'
   TATTACGTCCATGGACACGAAAGATTATCCTAG pTrpl

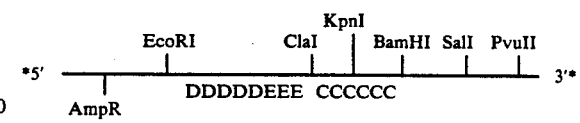

AmpR = Ampicillin resistance
D = Trp promoter/operator
E = Shine-Dalgarno sequence
C = Synthetic sequence

CHART 2

Construction of pTrp-BStm1

(a) pLG23 is cut with PvuII to isolate fragment 3 (494 bp).

Fragment 3

(b) pTrpl is treated with KpnI and Klenow to yield fragment 4 (4.3 kb).

Fragment 4

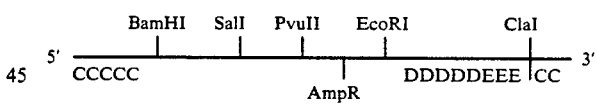

(c) Fragment 3 is ligated to fragment 4 to yield pTrp-BStm1. kb)

pTrp—BStml (4.8 kb)

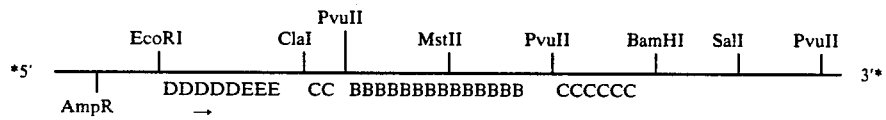

AmpR = Ampicillin resistance
D = Trp promoter/operator
E = Shine-Dalgarno sequence
C = Synthetic sequence
B = BSt sequence

CHART 3 pTrp-BStm1b (a) pTrp-BStm1 is cut with MstII and BamHI to isolate fragment 5 (4.8 kb).

Fragment 5

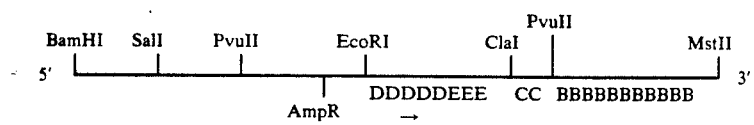

(b) Four oligonucleotides are assembled to yield fragment 6.

Fragment 6

(c) Fragment 6 is ligated to fragment 5 to yield pTrp-BStm1b pTrp—BStm1b (4.8 kb)

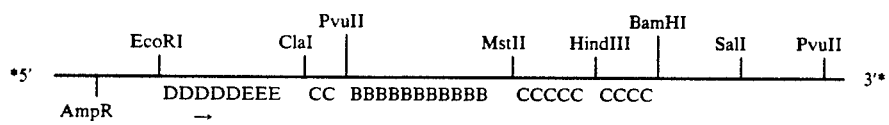

AmpR = Ampicillin resistance
D = Trp promoter/operator
E = Shine-Dalgarno
C = Synthetic sequence
B = BSt sequence

CHART 4
pTrp-BStm4

(a) pTrp-BStm1b is cut with MstII and ClaI to isolate fragment 7 (4.3 kb).

Fragment 7

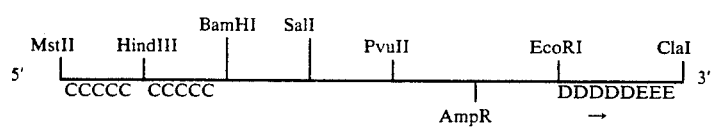

(b) pTrp-BStm1b is cut with PvuII and MstII to isolate fragment 8 (450 bp).

Fragment 8

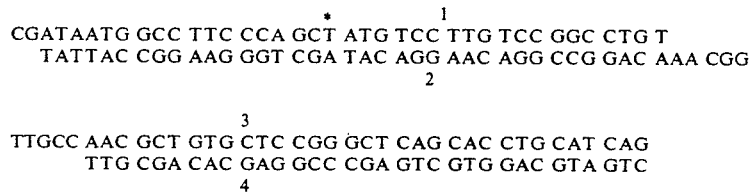

(c) Four oligonucleotides are assembled to yield fragment 9. Oligonucleotide 2 (Table 2)

```
                          *        1
CGATAATG GCC TTC CCA GCT ATG TCC TTG TCC GGC CTG T
    TATTAC CGG AAG GGT CGA TAC AGG AAC AGG CCG GAC AAA CGG
                                                      2

3
TTGCC AAC GCT GTG CTC CGG GCT CAG CAC CTG CAT CAG
  TTG CGA CAC GAG GCC CGA GTC GTG GAC GTA GTC
                                              4
```

(d) Fragments 7, 8 and 9 are ligated to yield pTrp-BStm4 (4.8 kb).

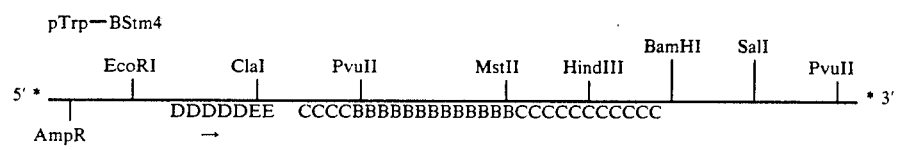

AmpR = Ampicillin resistance
D = Trp promoter/operator
E = Shine-Dalgarno sequence C = Synthetic sequence
B = BSt sequence

CHART 5

Construction of p50-BStm4

(a) Plasmid pBEU50 was digested with EcoRI and BamHI and the large 10 kb fragment 10 is gel isolated.

pBEU50

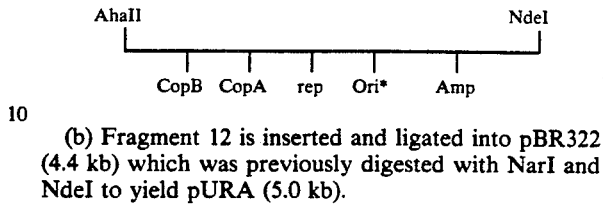

(b) Fragment 12 is inserted and ligated into pBR322 (4.4 kb) which was previously digested with NarI and NdeI to yield pURA (5.0 kb).

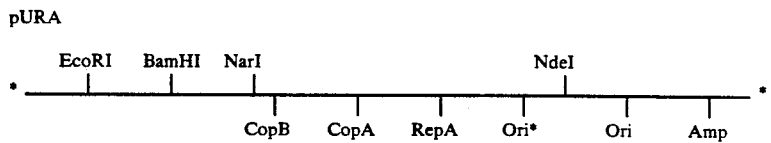

CopB = Gene to regulate RepA
CopA = Gene to regulate RepA
RepA = Gene to initiate runaway replication
Ori* = Runaway relicon from pBEU-17
Ori = Replicon from pBR322
Amp = Ampicillin resistance

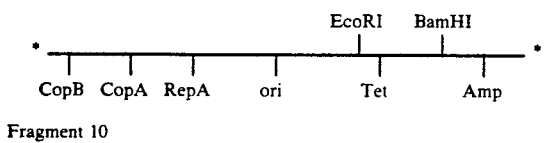

Fragment 10

(b) Plasmid pTrp-BStm4 (Chart 4) was digested with EcoRI and BamHI to yield fragment 11 (0.872 kb) which is gel isolated.

Fragment 11

EcoRI                                                            BamHI
|DDDDDEEECCCBBBBBBBBBBBBBBBBBBBBCCC          |

(c) Fragments 10 and 11 are annealed and ligated using T4 ligase to obtain p50-BStm4.

Amp = Ampillicin resistance
D = Trp promoter/operator
E = Shine-Dalgarno sequence
C = Synthetic sequence
B = BSt sequence
CopB = Gene to regulate RepA
CopA = Gene to regulate RepA
RepA = Gene to initiate runaway replication
Ori = Replicon from pBR322.

CHART 6

Construction of pURA (a) Vector pBEU-17 (13.8 kb) was digested with AhaII and NdeI to yield fragment 12 (2.4 kb).

CHART 7

Construction of pURA-m4

(a) p50-BStm4 (Chart 5) is digested with EcoRI and BamHI to yield fragment 13 (875 bp) containing the Trp promoter and rBSt gene.

Fragment 13

EcoRI                        BamHI
|DDDEEECCCBBBCCC     |

(b) pVV202T is digested with BamHI to yield fragment 14 (350 bp) containing a transcription terminator.

Fragment 14

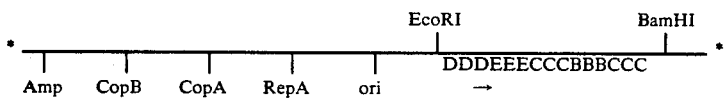

(c) pURA (Chart 6) is digested with EcoRI and BamHI to yield fragment 15 (4.6 kb) and ligated with fragments 13 and 14 to yield pURA-m4 (5.8 kb).

pURA—m4

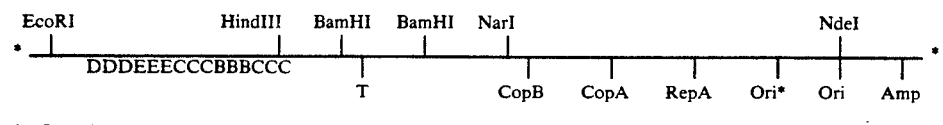

CopB = Gene to regulate RepA
CopA = Gene to regulate RepA
RepA = Gene to initiate runaway replication
Ori* = Runaway replicon from pBEU-17
Ori = Replicon from pBR322
Amp = Ampicillin resistance
T = Transcription terminator

CHART 8

Construction of pTrp-conSD (a) pSK4 is treated with HindIII, BAP and HpaI to obtain fragment 16 (4.6 kb).

Fragment 16

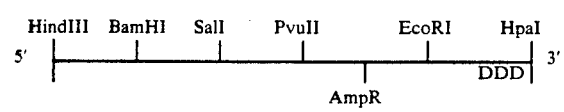

(b) The synthetic sequence of double-stranded DNA fragment 17 is ligated to fragment 18 to yield pTrp-conSD (4.6 kb).

Fragment 17

```
         1                          3
AACTAGTACGCAAGTTCACGTAAGGAG GATATCGATAATGGGTACCA
TTGATCATGCGTTCAAGTGCATT CCTCCTATAGCTATTACCCATGGTTCGA
         2                          4
``` pTrp—conSD (4.6 kb)

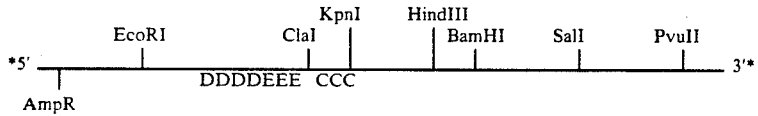

AmpR = Ampicillin resistance
D = Trp promoter/operator
E = Shine Dalgarno
C = Synthetic sequence

CHART 9 pTrp-PSt1

(a) pTrp-conSD is treated with KpnI, Klenow and ClaI to obtain fragment 18 (4.6 kb).

Fragment 18

```
     KpnI  BamHI  SalI   PvuII   EcoRI  HpaI   ClaI
5'  ├──────┼──────┼──────┼──────┼──────┼──────┤ 3'
                              DDDDEEE
              AmpR
```

(b) A PstI fragment (900 bp) containing the full length cDNA of PSt is isolated (Fragment 19). Fragment 19 is treated with Klenow and HgiA1 to isolate fragment 20 (660 bp).

Fragment 20

```
     HgiA1           SmaI        PvuII      PstI
5'  ├──────┼──────────┼────────────┼──────────┤
     PPPPPPPPPPPPPPPPPPPPPPPPPPPPPPPPPPPPPP
```

(c) The synthetic sequence of double-stranded DNA fragment 21 is ligated to fragments 19 and 20 to yield pTrp-PSt1.

Fragment 21

5' CGATAATGGCCTTCCCAGCTATGCCCTTGTCCAGCCTATTTGCCAACGCCGTGCT
   TATTACCGGAAGGGTCGATACGGGAACAGGTCGGATAAACGGTTGCGGC    3' pTrp—PSt1

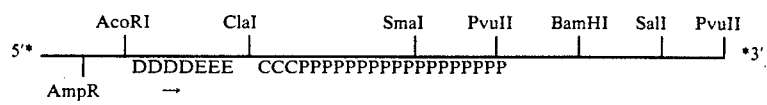

AmpR = Ampicillin resistance
D = Trp promoter/operator
E = Shine-Dalgarno sequence
C = Synthetic sequence P = Porcine somatotropin

CHART 10

Construction of pURA/PSt1

(a) Plasmid pURA is digested with EcoRI and BamHI and fragment 22 is isolated.

Fragment 22

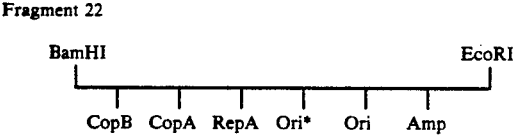

(b) Plasmid pTrp-PSt1 is cut with EcoRI and BamHI and fragment 23 (900 bp) is isolated. Fragments 22 and 23 are ligated to form pURA/PSt1.

pURA/PSt1

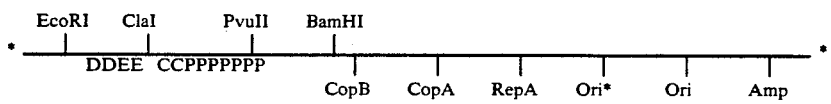

Amp = Ampicillin resistance
D = Trp promoter/operator
E = Shine-Dalgarno sequence
C = Synthetic sequence
P = Porcine growth hormone
CopB = Gene to regulate RepA
CopA = Gene to regulate RepA
RepA = Gene to initiate runaway replication
Ori* = Runaway replicon from pBEU-17
Ori = Replicon from pBR322

CHART 11 pTrp-trpL-PStc and pTrp-trpL-PSt1 a) pTrp1 (Chart 1) is treated with KpnI, Klenow and ClaI to obtain fragment 24 (4.6 kb).

Fragment 24

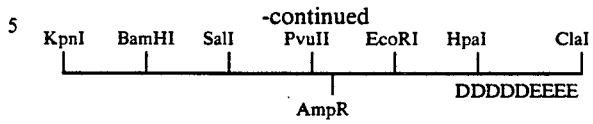

b) A PstI fragment (900 bp) containing the full length cDNA of PSt is isolated (Fragment 19). Fragment 19 is treated with Klenow and HgiA1 to generate fragment 20 (660 bp).

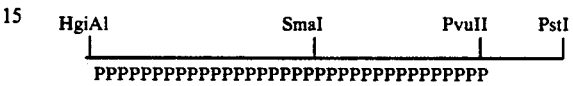

c) The synthetic sequence of double-stranded DNA fragment 25 is ligated to fragments 24 and 20 to yield pTrp-trpL-PSt1 and the synthetic fragment of double-stranded DNA fragment 26 is ligated to fragments 24 and 20 to yield pTrp-trpL-PStc.

Fragment 25

```
5' CGATAATGGCCTTCCCAGCTATGCCCTTGTCCAGCCTATTTGCCAACGCCGTGCT
   TATTACCGGAAGGGTCGATACGGGAACAGGTCGGATAAACGGTTGCGGC         3'
```

Fragment 26

```
5' CGATAATGGCCTTCCCAGCCATGCCCTTGTCCAGCCTATTTGCCAACGCCGTGCT
   TATTACCGGAAGGGTCGGTACGGGAACAGGTCGGATAAACGGTTGCGGC         3'
``` pTrp—trpl—PStc and pTrp—trpL—PSt1

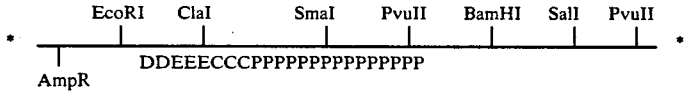

AmpR = Ampicillin resistance
D = Trp promoter/operator
E = TrpL Shine-Delgarno sequence
C = Synthetic sequence
P = Porcine somatotropin

CHART 12

Construction of pURA-trpL-PStc and pURA-trpL-PSt1 a) Plasmid pURA is digested with EcoRI and BamHI and fragment 22 (Chart 10) is isolated.

Fragment 22

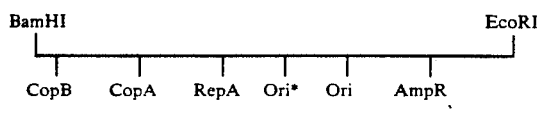

b) Plasmids pTrp-trpL-PStc and pTrp-trpL-PStl are cut with EcoRI and BamHI and fragments 27 and 28 (900 bp) are isolated. Fragments 22 and 27 are ligated to form pURA-trpL-PStc. Fragments 22 and 28 are ligated to form pURA-trpL-PStl. Both vectors which differ by a single base pair can be represented as shown below.

pURA—trpL—PStc or pURA—trpL—PStl

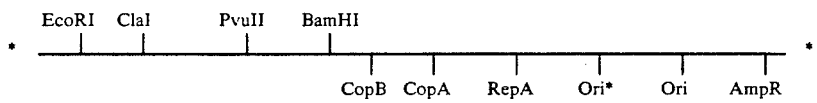

Amp = Ampicillin resistance
D = Trp promoter/operator
E = TrpL Shine-delgarno sequence
C = Synthetic sequence
P = Porcine somatotropin
CopB = Gene to regulates RepA
CopA = Gene to regulate RepA
RepA = Gene to initiate replicon runaway replication
Ori* = Runaway replicon from pBEU-17
Ori = Replicon from pBR322

CHART 13

Deletion of the pURA-m1 Gene (a) Plasmid pURA-M4 (Chart 7) was digested with EcoRI and HindIII and the overhanging 5'-ends were blunted by filling with Klenow fragment and dNTP's to generate fragment 29.

Fragment 29

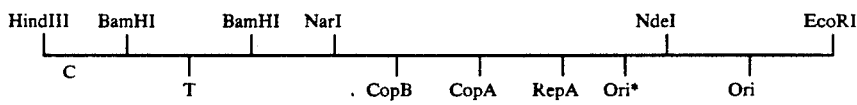

(b) Fragment 29 was ligated to yield pURA4 $\Delta bgh_{E/H}$.

pURA4 $\Delta bgh_{E/H}$

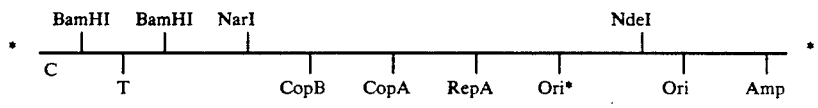

C = Synthetic BSt sequence
T = Transcription terminator
CopB = Gene to regulate RepA
CopA = Gene to regulate RepA
RepA = Gene to initiate runaway
Ori* = Origin of replication from pBEU-17
Ori = Origin of replication from pBR322
Amp = Ampicillin resistance

CHART 14

Plasmid pTrp-conSD-HC-IL1-1

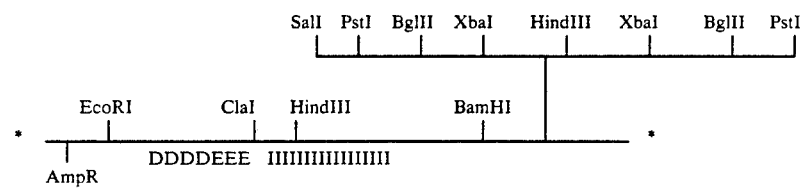

AmpR = ampicillin resistance
D = Trp promoter/operator
E = Shine-Dalgarno sequence
I = IL-1β gene

We claim:
1. An expression plasmid capable of runaway at a constant temperature below 34° C. which is useful for transforming a host cell and permitting the host cell to produce a heterologous protein, which plasmid comprises a mutant R1 replicon from pBEU-17, an orgin of replication from pBR322, and a cDNA encoding the heterologous protein.

2. A plasmid according to claim 1, wherein the host cell is *E. coli* and the cDNA encodes a bovine or porcine somatotropin.

3. A plasmid according to claim 2, wherein the first four codons of the cDNA are selected from the group consisting of:

GCC TTC CCA GCT,

GCT TTC CCA GCT,

ACC TTC CCA GCC,

GCC TTC CCA GTC,

AAA TTC CCA GCC,

TTC TTC CCA GCC, and

TTC CCA GCC ATG.

4. A plasmid according to claim 3 wherein the first four codons of the cDNA are GCC TTC CCA GCT.

5. An *E. coli* host cell comprising a mutation of the rpoH112 allele or hflB29 allele, and a plasmid of claim 1.

6. A host cell according to claim 5 wherein the mutation is the rpoH112 allele.

7. A host cell according to claim 5 wherein the mutation is the hflB29 allele.

8. An *E. coli* host cell comprising a mutation of the rpoH112 allele or hflB29 allele, and a plasmid of claim 3.

9. A host cell according to claim 8 wherein the mutation is the rpoH112 allele.

10. A host cell according to claim 8 wherein the mutation is the hflB29 allele.

11. A host cell according to claim 8 wherein the mutation is the hflB29 allele and the first four codons of the cDNA are GCC TTC CCA GCT.

12. A host cell according to claim 8 wherein the plasmid encodes porcine somatotropin.

13. A method of expressing a heterologous gene comprising culturing a host cell according to claim 5.

14. A method of expressing a heterologous gene comprising culturing a host cell according to claim 8.

15. *E. coli* host cell BST-1C (NRRL B-18303) or D112 (NRRL B-18168).

16. The *E. coli* host cell according to claim 15 which is BST-1C (NRRL B-18303).

* * * * *

UNITED STATES PATENT AND TRADEMARK OFFICE
CERTIFICATE OF CORRECTION

PATENT NO. : 5,240,837

DATED : August 31, 1993

INVENTOR(S) : Che-Shen C. Tomich

It is certified that error appears in the above-indentified patent and that said Letters Patent is hereby corrected as shown below:

On the title page: Item [56]

under References cited, the listing of Foreign Patent Documents should include -- 047600 8/1981 European Patent Off. --

Column 31, line 60, "AcoRI" should read -- EcoRI --

Signed and Sealed this

Twentieth Day of December, 1994

Attest:

BRUCE LEHMAN

*Attesting Officer*　　　　　*Commissioner of Patents and Trademarks*